US012544146B2

(12) United States Patent
Blackwell

(10) Patent No.: US 12,544,146 B2
(45) Date of Patent: Feb. 10, 2026

(54) APPARATUS AND METHOD FOR REMOVING CIRCULAR TRACKERS ATTACHED TO A TRACKING ARRAY

(71) Applicant: GLOBUS MEDICAL, INC., Audubon, PA (US)

(72) Inventor: Timothy J. Blackwell, Ft. Pierce, FL (US)

(73) Assignee: Globus Medical, Inc., Audubon, PA (US)

( * ) Notice: Subject to any disclaimer, the term of this patent is extended or adjusted under 35 U.S.C. 154(b) by 1022 days.

(21) Appl. No.: 17/670,062

(22) Filed: Feb. 11, 2022

(65) Prior Publication Data

US 2023/0255693 A1 Aug. 17, 2023

(51) Int. Cl.
*A61B 34/20* (2016.01)
*A61B 90/00* (2016.01)

(52) U.S. Cl.
CPC .............. *A61B 34/20* (2016.02); *A61B 90/00* (2016.02)

(58) Field of Classification Search
CPC .......... A61B 34/20; A61B 90/00; A61B 90/39
USPC .............................................................. 606/1
See application file for complete search history.

(56) References Cited

U.S. PATENT DOCUMENTS 4,150,293 A 4/1979 Franke
5,246,010 A 9/1993 Gazzara et al.
5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
(Continued)

OTHER PUBLICATIONS

US 8,231,638 B2, 07/2012, Swarup et al. (withdrawn)

*Primary Examiner* — Nadia A Mahmood

(57) ABSTRACT

A tool for removing circular trackers attached to tracking array posts. The tool includes a tubular body and a driver tube sized to be received in the tubular body. The distal portion of the tubular body and driver tube has respective first and second apertures that are circumferentially partially open in a lateral direction for receiving the circular tracker. The two apertures cooperate with each other such that when the second aperture is rotated relative to the first aperture, the circular tracker is enclosed within the driver tube and the tubular body for removal without pulling on the tracking array or the post.

12 Claims, 6 Drawing Sheets

(56) References Cited

U.S. PATENT DOCUMENTS

| | | | |
|---|---|---|---|
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |
| 7,683,331 | B2 | 3/2010 | Chang |
| 7,683,332 | B2 | 3/2010 | Chang |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,711,406 | B2 | 5/2010 | Kuhn et al. |
| 7,720,523 | B2 | 5/2010 | Omernick et al. |
| 7,725,253 | B2 | 5/2010 | Foxlin |
| 7,726,171 | B2 | 6/2010 | Langlotz et al. |
| 7,742,801 | B2 | 6/2010 | Neubauer et al. |
| 7,751,865 | B2 | 7/2010 | Jascob et al. |
| 7,760,849 | B2 | 7/2010 | Zhang |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,796,728 | B2 | 9/2010 | Bergfjord |
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,853,313 | B2 | 12/2010 | Thompson |
| 7,865,269 | B2 | 1/2011 | Prisco et al. |
| D631,966 | S | 2/2011 | Perloff et al. |

(56) References Cited

U.S. PATENT DOCUMENTS 7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Williams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Isaacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.

(56) References Cited

U.S. PATENT DOCUMENTS 8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 Von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 Von Jako
2008/0109012 A1 5/2008 Falco et al.
2008/0144906 A1 6/2008 Allred et al.
2008/0161680 A1 7/2008 Von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.

(56) References Cited

U.S. PATENT DOCUMENTS

2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.

(56) References Cited

U.S. PATENT DOCUMENTS

| | | | |
|---|---|---|---|
| 2014/0303434 | A1 | 10/2014 | Farritor et al. |
| 2014/0303643 | A1 | 10/2014 | Ha et al. |
| 2014/0305995 | A1 | 10/2014 | Shelton, IV et al. |
| 2014/0309659 | A1 | 10/2014 | Roh et al. |
| 2014/0316436 | A1 | 10/2014 | Bar et al. |
| 2014/0323803 | A1 | 10/2014 | Hoffman et al. |
| 2014/0324070 | A1 | 10/2014 | Min et al. |
| 2014/0330288 | A1 | 11/2014 | Date et al. |
| 2014/0364720 | A1 | 12/2014 | Darrow et al. |
| 2014/0371577 | A1 | 12/2014 | Maillet et al. |
| 2015/0039034 | A1 | 2/2015 | Frankel et al. |
| 2015/0085970 | A1 | 3/2015 | Bouhnik et al. |
| 2015/0146847 | A1 | 5/2015 | Liu |
| 2015/0150524 | A1 | 6/2015 | Yorkston et al. |
| 2015/0196261 | A1 | 7/2015 | Funk |
| 2015/0213633 | A1 | 7/2015 | Chang et al. |
| 2015/0335480 | A1 | 11/2015 | Alvarez et al. |
| 2015/0342647 | A1 | 12/2015 | Frankel et al. |
| 2016/0005194 | A1 | 1/2016 | Schretter et al. |
| 2016/0166329 | A1 | 6/2016 | Langan et al. |
| 2016/0235480 | A1 | 8/2016 | Scholl et al. |
| 2016/0249990 | A1 | 9/2016 | Glozman et al. |
| 2016/0302871 | A1 | 10/2016 | Gregerson et al. |
| 2016/0320322 | A1 | 11/2016 | Suzuki |
| 2016/0331335 | A1 | 11/2016 | Gregerson et al. |
| 2017/0135770 | A1 | 5/2017 | Scholl et al. |
| 2017/0143284 | A1 | 5/2017 | Sehnert et al. |
| 2017/0143426 | A1 | 5/2017 | Isaacs et al. |
| 2017/0156816 | A1 | 6/2017 | Ibrahim |
| 2017/0202629 | A1 | 7/2017 | Maillet et al. |
| 2017/0212723 | A1 | 7/2017 | Atarot et al. |
| 2017/0215825 | A1 | 8/2017 | Johnson et al. |
| 2017/0215826 | A1 | 8/2017 | Johnson et al. |
| 2017/0215827 | A1 | 8/2017 | Johnson et al. |
| 2017/0231710 | A1 | 8/2017 | Scholl et al. |
| 2017/0258426 | A1 | 9/2017 | Risher-Kelly et al. |
| 2017/0273748 | A1 | 9/2017 | Hourtash et al. |
| 2017/0296277 | A1 | 10/2017 | Hourtash et al. |
| 2017/0360493 | A1 | 12/2017 | Zucher et al. |
| 2021/0236212 | A1 * | 8/2021 | Ghanam .................. G06T 7/20 |

* cited by examiner

APPARATUS AND METHOD FOR REMOVING CIRCULAR TRACKERS ATTACHED TO A TRACKING ARRAY

FIELD

The present disclosure generally relates to optical tracking systems and more particularly a tool for removing circular trackers attached to a tracking array.

BACKGROUND

Tracking arrays attached to a patient are used to track the patient body parts in navigation assisted surgeries. Typically, the circular or spherical reflective trackers are snapped onto metal posts projecting upwardly from the tracking array.

Often, there is a need to replace one or more defective trackers attached to the tracking array while a navigation assisted or robotically assisted surgery is being performed. Removing the trackers by hand needs to be done very carefully so as not to disturb the tracking array itself. If there is sufficient movement of the tracking array, it may cause the system to lose tracking registration and consequently, the entire time-consuming registration of the tracking array relative to the patient needs to be redone.

Accordingly, there is a need for an improved apparatus and method for removing the trackers without disturbing the tracking array which is already attached to the patient body.

SUMMARY

A tool for removing circular trackers attached to tracking array posts. The tool includes a tubular body and a driver tube sized to be received in the tubular body. The distal portion of the tubular body and driver tube has respective first and second apertures that are circumferentially partially open in a lateral direction for receiving the circular tracker. The two apertures cooperate with each other such that when the second aperture is rotated relative to the first aperture, the driver tube slides upwardly relative to the tubular body so as to lift the circular tracker from the post.

Since the pulling force is applied to the circular tracker relative to the tubular body, the tracker is removed without any force applied to the tracking array so as to minimize the chance of losing registration. Also, since the two apertures close to capture the tracker, the chance of losing the removed tracker in the patient body is substantially reduced.

DETAILED DESCRIPTION OF THE ILLUSTRATED EMBODIMENTS

Figure 1:
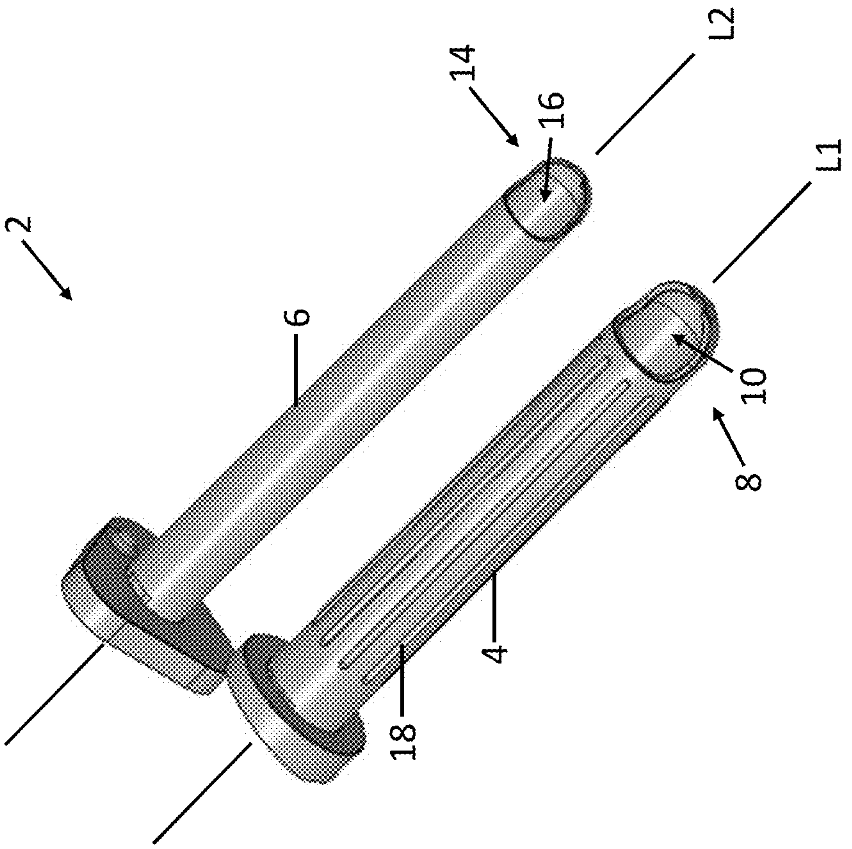
FIG. 1 is a perspective view of both parts in same orientation.

FIG. 1 illustrates a perspective view of a removal tool 2 for removing circular trackers 12 that are attached to a tracking array 38 according to one aspect of the present invention. The removal tool 2 includes a tubular body 4 and a driver tube 6. The distal portion 8 of the tubular body 4 has a first aperture 10 which is circumferentially partially open (e.g., 180 degrees as shown) in lateral and longitudinal (downward) directions relative to a longitudinal axis L1 defined by the tube. The first aperture 10 receives the circular tracker 12 to be removed as will be explained in more detail later herein. Longitudinal grooves 18 formed on the exterior surface of the tubular body 4 provides extra grip for holding the body by a user's hand. The grooves 18 are circumferentially and uniformly spaced from each other.

The driver tube 6 is sized to be slidably received in the tubular body 4. Its distal portion 14 has a second aperture 16, which is also circumferentially partially open (e.g., 180 degrees as shown) in lateral and longitudinal (downward) directions relative to its longitudinal axis L2, the first and second apertures 8,14 cooperate with each other such that when the second aperture 16 is rotated relative to the first aperture 10, the driver tube 6 slides upwardly to pull the circular tracker off the post 36 of the tracking array 38 and simultaneously encloses the tracker within the driver and the tubular body 4 for removal.

The tubular body 4 at its proximal portion includes a flange 34 having a ramped surface 20 and the driver tube 6 at its proximal portion includes a triangle-shaped flange 22. The flange 22 of the driver tube 6 rides on the ramped surface 20 of the flange 34 to slide upwardly upon rotation of the driver tube 6 relative to the tubular body 4. The sliding movement causes the driver tube 6 to pull the circular tracker from the post 36. In the embodiment shown, a downwardly extending partially round projection 24 of the flange 22 is adapted to ride on the ramped surface 20.

Figure 2B:
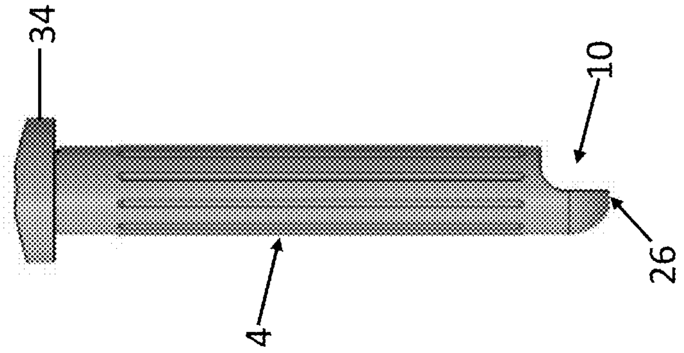
FIG. 2B is a side view of the main tubular body at 90 degree offset from that of FIG. 2A to show the side aperture pointing to the left.
Figure 2A:
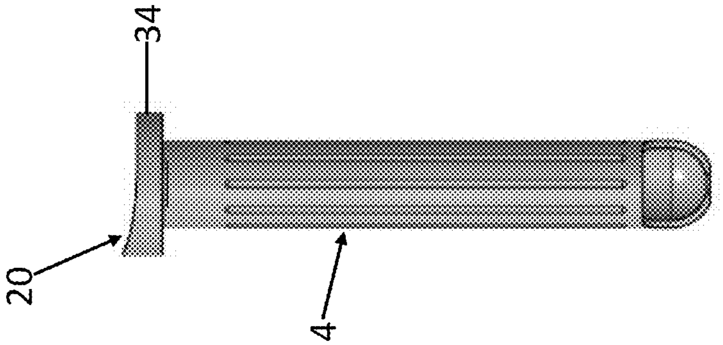
FIG. 2A is a side view of the main tubular body showing the side aperture in full 180 degrees.
Figure 3:
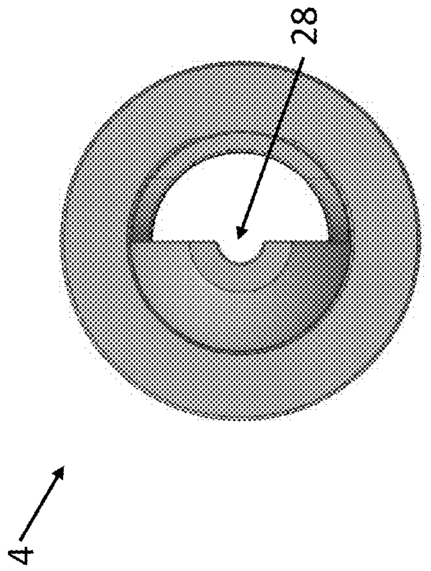
FIG. 3 is a bottom view of the tubular body of FIG. 2A.
Figure 4B:
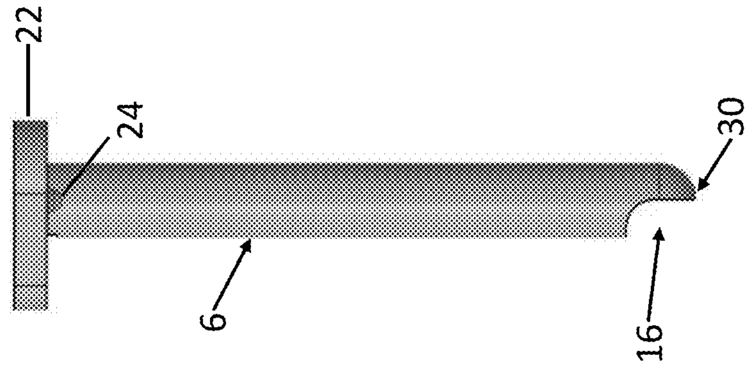
FIG. 4B is a side view of the driver tube at 90 degree offset from that of FIG. 4A to show the side aperture pointing to the left.
Figure 4A:
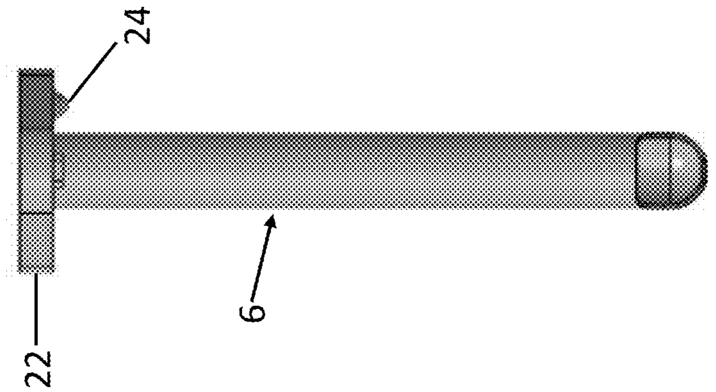
FIG. 4A is a side view of the driver tube showing the side aperture in full 180 degrees.

The distal portion 8 of the tubular body 4 as shown in FIGS. 2A-3 includes a partially open bottom surface 26 which has a central recess 28 adapted for partially surrounding the post 36. Similarly, the distal portion 14 of the driver tube 6 also has a partially open bottom surface 30 having a central recess 32 adapted for partially surrounding the post 36.

Figure 6:
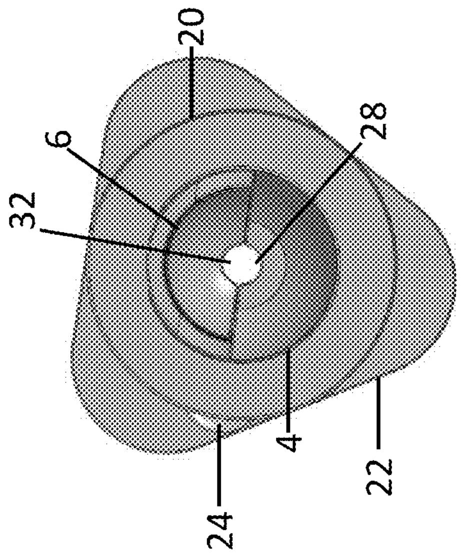
FIG. 6 is a bottom view of the driver tube inside the tubular body showing a closed aperture.
Figure 5:
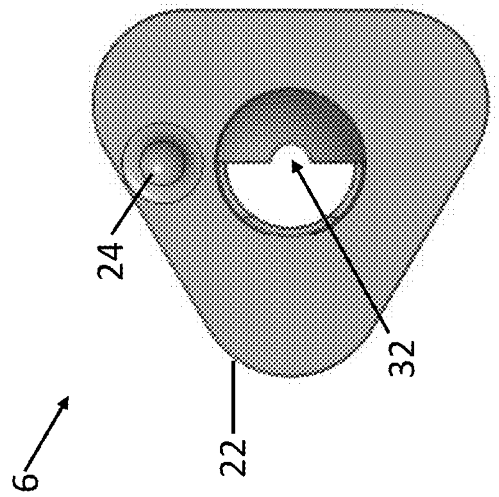
FIG. 5 is a bottom view of the driver tube inside the tubular body of FIG. 4A.
Figure 7:
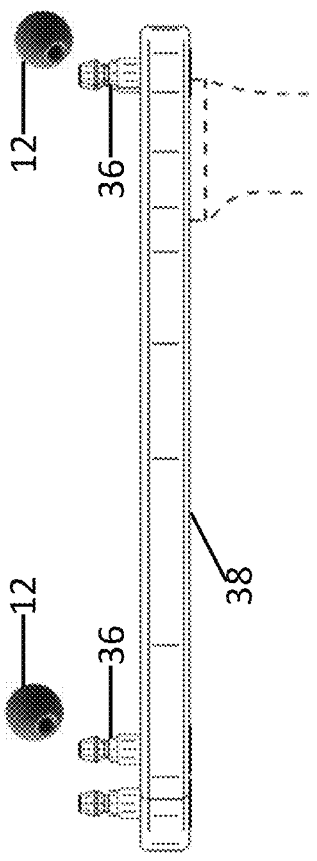
FIG. 7 is a side view of a tracking array with a spherical tracker.

The ramped surface 20 is shaped such that rotation of the driver tube 6 in either direction causes the driver tube 6 to slide upwardly as the projection 24 rotates toward the highest point of the ramped surface 20. When the projection 24 is resting on the highest point of the ramped surface 20, the first and second apertures 10,14 face each other to enclose the circular tracker 12 as shown in FIG. 6.

The aperture of each of the tubular body 4 and the driver tube 6 is circumferentially open by at least 150 degrees. As shown, the apertures are open 180 degrees circumferentially.

In operation, the driver tube 6 is inserted into the tubular body 4 until the projection 24 of the flange 22 bottoms out and contacts the ramped surface 20. The projection 24 should be rotated away from the highest point in the ramped surface 20 until the first and second apertures 10,14 are nested and aligned so that they are pointed in the same direction.

The nested distal portions 8,14 of the tool 2 are then placed on the side of the circular tracker 12 to be removed.

The tracker 12 is attached to the post 36 of the tracking array 38 which itself is attached to a patient bone. While the central recesses 28,32 contact the post 36, the driver tube 6 is rotated. As the driver tube 6 rotates, the tracker 12 is pulled off the post 36 and is captured by the closed apertures. Since the tracker 12 is pulled by the driver tube 6 relative to the tubular body 4, the tracker 12 can be removed without any force being applied to the tracking array 38. Also, closing of the apertures from rotation of the driver tube 6 avoids dropping the tracker 12 into the surgical site. The removed tracker 12 can then be discarded away from the surgical site.

While it is apparent that the invention disclosed herein is well calculated to fulfill the objects stated above, it will be appreciated that numerous modifications and embodiments may be devised by those skilled in the art. While devices and methods are described in terms of "comprising," "containing," "having," or "including" various elements or steps, the devices and methods can also "consist essentially of" or "consist of" the various elements and steps.

What is claimed is:

1. A removal tool for a circular tracker attached to a post of a tracking array comprising:

a tubular body including a distal portion having a first aperture, the first aperture being circumferentially partially open in a lateral direction for receiving the circular tracker; and a driver sized to be received in the tubular body and including a distal portion having a second aperture, the second aperture being circumferentially partially open in a lateral direction, the first and second aperture cooperating with each other such that when the second aperture is rotated relative to the first aperture, the circular tracker is enclosed within the driver and the tubular body for removal, wherein the driver slides upwardly to pull the attached circular tracker from the post upon rotation of the driver relative to the tubular body.

2. The removal tool of claim 1, wherein the driver slides upwardly to pull the attached circular tracker from the post upon rotation of the driver relative to the tubular body.

3. The removal tool of claim 1, wherein the tubular body includes a ramped surface and a portion of the driver rides on the ramped surface to slide upwardly upon rotation of the driver relative to the tubular body.

4. The removal tool of claim 1, wherein the tubular body includes a ramped surface and the driver includes a flange adapted to rotate against the ramped surface such that the driver slides upwardly to pull the attached circular tracker from the post.

5. The removal tool of claim 4, wherein the flange includes a downwardly extending projection adapted to ride on the ramped surface.

6. The removal tool of claim 1, wherein the distal portion of the tubular body includes a partially open bottom surface below the aperture.

7. The removal tool of claim 6, wherein the distal portion has a bottom surface having a central recess adapted for partially surrounding the post.

8. The removal tool of claim 1, wherein each distal portion of the driver and the tubular body has a bottom surface having a central recess adapted for partially surrounding the post.

9. The removal tool of claim 1, wherein the tubular body has a flange having a ramped upper surface.

10. The removal tool of claim 1, wherein the tubular body has a flange having a ramped upper surface and the driver includes a flange whose bottom surface is adapted to rotate against the ramped upper surface such that driver slides upwardly to pull the circular tracker from the post upon rotation of the driver relative to the tubular body in either circumferential direction.

11. The removal tool of claim 1, wherein each distal portion of the tubular body and the driver includes a partially closed bottom surface and a central recess.

12. The removal tool of claim 1, wherein the aperture of each of the tubular body and the driver is circumferentially open by at least 150 degrees.

* * * * *